United States Patent [19]

Yamashita et al.

[11] Patent Number: 4,778,593

[45] Date of Patent: Oct. 18, 1988

[54] METHOD AND APPARATUS FOR DISCRIMINATING MINUTE PARTICLES

[75] Inventors: Mikio Yamashita; Takuzo Sato, both of Ibaraki; Yoshio Noguchi, Matsudo; Yoshinobu Uchibori, Ibaraki; Akio Shinohara, Fujisawa; Hiroshi Soga, Yamato; Sadayuki Miyazaki, Tokyo, all of Japan

[73] Assignees: Agency of Industrial Science and Technology; Showa Denko Kabushiki Kaisha, both of Tokyo, Japan

[21] Appl. No.: 859,203

[22] Filed: Apr. 28, 1986

Related U.S. Application Data

[63] Continuation of Ser. No. 592,777, Mar. 26, 1984, abandoned.

[30] Foreign Application Priority Data

Mar. 25, 1983 [JP] Japan .................... 53-48674

[51] Int. Cl.$^4$ ............. B07C 5/342; G01N 21/64; G01N 33/48
[52] U.S. Cl. ................. 209/3.1; 209/579; 250/461.2; 356/39
[58] Field of Search ............. 209/3.1-3.3, 209/579; 250/461.2, 213 VT; 356/39, 72, 73, 317, 318; 358/93

[56] References Cited

U.S. PATENT DOCUMENTS

| | | | |
|---|---|---|---|
| 3,710,933 | 1/1973 | Fulwyler et al. | 209/3.1 |
| 4,006,360 | 2/1977 | Mueller | 250/461.2 |
| 4,049,970 | 9/1977 | Ford | 250/461.2 |
| 4,058,732 | 11/1977 | Wieder . | |
| 4,198,567 | 4/1980 | Eneroth et al. . | |
| 4,212,397 | 7/1980 | Bockelmann | 209/589 |
| 4,232,333 | 11/1980 | Hiruma et al. | 358/93 |
| 4,327,285 | 4/1982 | Bradley et al. | 250/213 VT |
| 4,435,727 | 3/1984 | Schiller et al. | 358/107 X |
| 4,444,317 | 4/1984 | Wick et al. | 209/3.1 |

FOREIGN PATENT DOCUMENTS 46-27118 8/1971 Japan .
56-13266 3/1981 Japan .

OTHER PUBLICATIONS

"A Survey of Present State of Various Flow Cytometers", Y. Noguchi, Denshi Gijutsu Sogo Kenkyusho Iho, vol. 44, No. 3, 1980.

Primary Examiner—Robert B. Reeves
Assistant Examiner—Edward M. Wacyra
Attorney, Agent, or Firm—Sughrue, Mion, Zinn, Macpeak & Seas

[57] ABSTRACT

In order to discriminate minute particles such as biological particles or organic polymers, a suspension of minute particles is formed into a particle stream with the individual particles substantially separated from each other, the particle stream is irradiated with a high-intensity light beam, the particle stream irradiated with the high-intensity light beam is formed into droplets, and the particle in each droplet is discriminated in accordance with the intensity of light emited from the particle upon irradiation with the high-intensity light beam. In discriminating the particles, a high-intensity light pulse is used as the high-intensity light beam, and each minute particle is discriminated in accordance with a change in the emitted light intensity over a period of time.

6 Claims, 9 Drawing Sheets

METHOD AND APPARATUS FOR DISCRIMINATING MINUTE PARTICLES

This is a continuation of application Ser. No. 592,777, filed Mar. 26, 1984, now abandoned.

BACKGROUND OF THE INVENTION

1. Field of the Invention

The present invention relates to a method and apparatus for discriminating (sorting or selecting) minute particles such as organic polymers or biological particles, e.g., polymers in cells. More particularly, the present invention relates to a method and apparatus wherein a light pulse of a high-intensity light beam such as a laser beam is irradiated onto a continuous flow of minute particles in suspension to cause the minute particles to emit fluorescence or phosphorescence; a change in the intensity of emitted light over a period of time is automatically measured and analyzed to discriminate the minute particles; and the minute particles are physically sorted in accordance with the discrimination result.

2. Description of the Prior Art

In cytology, there is an increasing demand for automatic cell analysis and sorting. Presently, the screening of cytological materials to detect, for example, cancerous or malignant cells, is typically performed using a hierarchy of two or more levels of screening. First, cell samples are visually prescreened by an observer to search out those that appear to contain abnormal cells. These samples are then later examined by a trained cytotechnologist or pathologist to determine whether the cells are indeed cancerous or malignant. Although this method works well, it is also subject to a number of disadvantages, i.e., it is time-consuming and requires a trained technician, thereby making the method costly. Furthermore, the method is nonquantitative, since the criteria of abnormality are largely subjective. Because of the time and cost, it is difficult to apply this method to very large cell populations.

For the analysis of biological minute particles, flow system analysis is called flow cytometery. This method has the potential to provide some solution to the above problems. In flow cytometry, an optical or electrical signal is obtained which represents information on cell suspension, and cell properties or structures are analyzed in accordance with such a signal. In a flow cytometer based on flow cytometry, light is irradiated onto a cell suspension flowing at high speed in a very small detection volume, and an optical signal or electrical signal is obtained from information returned from the cell. Flow cytometry thus allows the discrimination of normal and abnormal cells within a short period of time, and provides quick automatic cell screening.

A continuous laser beam is used as the irradiating light. However, a single parameter such as cell size is frequently insufficient to allow correct cell analysis. In view of this, multiparameter analysis involving light absorption, fluorescence, scatter, and the like is presently performed. Cell size is used as a parameter when cells of a particular type have different sizes in normal and abnormal states. Thus, normal cells can be differentiated from abnormal cells by observing the cell size. When a particular type of cell does not allow discrimination between normal and abnormal cells, using only the cell size as a parameter, an additional parameter which does allow such discrimination is used. Thus, multiparameter analysis increases the ability to distinguish differences between cells of a particular type.

A cell sorter not only sorts minute particles in accordance with optical or electrical signals representing particular information on cells, but also performs cell grouping based on signal processing, such as grouping into normal and abnormal cells.

A flow cytometer and cell sorter are reported by Noguchi in Denshi Gijutsu Sogo Kenkyusho Iho, Vol. 44, No. 3 (1980). A cell sorter is also described in Japanese Examined Patent Publication (Kokoku) Nos. 46-27118 and 56-13266.

Unlike cell analysis under microscopic observation or by means of cell samples, in flow system analysis using a flow cytometer a large number of cells are allowed to flow and can be discriminated within a short period of time. This method allows statistical processing of the cells. However, a parameter has not been available that allows discrimination based on highly significant information directly related to the abnormality of cells, such as information on the cell morphology, molecular biological information, or molecular chemical information. Since such highly significant information is directly related to the occurrence of abnormalities in cells, its use improves the screening precision due to an increase in the number of parameters. This contributes greatly to clinical applications and fundamental medical studies.

The present inventors have studied the possibility of adding a new parameter to the conventional flow system analysis method that allows the discrimination of cells based on such highly significant information.

Meanwhile, in the field of laser technology, a technique of a short pulse train tunable laser is being established. With the recent advent of a dye laser or the like using a dye solution as a laser medium, a laser beam tunable to any wavelength within a wide range from ultraviolet to infrared rays can be obtained. The tunable laser can provide a light pulse of a very short duration.

The mode locking method is known as a method of obtaining such a short light pulse. Although various methods of achieving mode locking are known, the synchronous locking method is most frequently used. According to the synchronous locking method, a short light pulse from a mode-locked argon ion laser is used as an excitation light source for exciting a dye laser; the resonance period of a resonator in the dye laser is set to coincide with the period of the obtained pulse train; and the gain of the dye laser is periodically modulated to generate an ultra-short light pulse train.

When this mode locking method is used, a tunable light pulse train is obtained which has a pulsewidth of several nanoseconds ($10^{-9}$ seconds) to several picoseconds ($10^{-12}$ seconds) and has a high output, monochromatic property, and directivity. The period of the pulse train can be kept variable within a range of several milliseconds to several nanoseconds by the cavity damping method.

An output laser beam obtained by such a method generally comprises linearly polarized light, since an optical element used in the laser resonator is set at the Brewster angle and the excited laser beam is linearly polarized light.

When such light changing at high speed is irradiated onto a substance, to cause this substance to emit light, changes in the intensity of emitted light over a period of time also occur at high speed. This means that the observation or measurement of emitted light must be performed with high precision with respect to time.

When the observation unit time is longer than a subnanosecond, a change in the intensity of emitted light is converted into an electrical signal by a photosensor, such as a photodiode or a photoelectron multiplier, and the obtained electrical signal is processed as needed. The processed signal is supplied to an oscilloscope, for example, to display an image on a CRT monitor, or is counted by a photon counting method.

In the measurement of ultra high-speed time units such as a picosecond or subpicosecond, a photosensor as described above presents the problems of response speed and sensitivity. Therefore, a streak camera is used in this case. In order to measure slight, repetitive, and ultra high-speed changes in light intensity, a synchro scan streak camera can be conveniently used. In a streak camera, photoelectrons from a surface which receives emitted light are accelerated and deflected in such a manner that a change in the intensity of the received light is translated into a change in geometrical position of an image on a CRT monitor.

Attempts are being made to use a photochemically reactive substance such as a hemoglobin complex to measure a change in the intensity of transient emitted light over a period of time upon short pulse train laser excitation, as described above. The application of such a method to the analysis of biological polymers is also proposed, and is expected to be effective in the analysis of the local structure of such biological polymers. However, these subjects are still in the state of preliminary studies with cell samples.

In view of this situation, the present inventors have made studies to determine the plausibility of combining this method with flow system analysis, in order to allow on-line selecting and/or sorting of minute particles in accordance with a different in the local structure at the molecular level of minute particles such as biological particles or organic polymers.

SUMMARY OF THE INVENTION

It is an object of the present invention to provide a method and apparatus for the high-speed and high-precision discrimination of a large number of minute particles wherein a high-intensity light pulse is used as a high-intensity irradiation light beam, and a change in the intensity of emitted light from the particles over a period of time is measured, thereby allowing the discrimination of a large population of particles based on highly significant information obtained from the emission of light from the particles.

According to the present invention, there is provided, a method of sorting minute particles, comprising the steps of producing a stream of minute particles, in which substantially each of the minute particles is separated from the adjacent particle with an interval, from a suspension of the minute particles; irradiating the produced stream of minute particles with a high-intensity light beam; changing the irradiated stream of minute particles into a sequence of droplets; and discriminating the particle in each droplet by the intensity of light emission from the irradiated particle; high-intensity light pulses being used as the high-intensity light beam, and the discrimination being carried out on the basis of the change in the intensity of the emitted light over a period of time.

According to the present invention, there is also provided an apparatus for discriminating minute particles, comprising a flow chamber, a unit for introducing a suspension of the minute particles into the flow chamber and producing a particle stream with the individual particles being substantially separated from each other, a unit for generating a high-intensity light pulse, a unit for irradiating the produced particle stream with the high-intensity light pulse; a unit for changing the irradiated particle stream into a sequence of droplets; a unit for detecting light emission from the irradiated particle; and a unit for calculating the change in the intensity of the emitted light on the basis of the detection by the light emission detecting unit made over a period of time.

According to the method of the present invention, the techniques of the conventional flow system analysis method, tunable short pulse light, and high-speed optical phenomenon are combined into a high-speed real-time data processing technique, in which the selecting of minute particles and sorting of these minute particles in accordance with the selection result are performed.

In the method of the present invention, minute particles themselves, or a suspension thereof, with a dye bound thereto are formed into a fine stream. The stream is jetted from a nozzle into a jet stream and is then formed into droplets. The thin stream or jet stream is irradiated with a high-intensity light pulse tuned to an absorption band of the minute particles involved. Light emitted from the stream, such as fluorescence, is received. A change in intensity of a preselected type of emitted light or a combination of types thereof is measured at high speed, and the detected change is compared with a reference value corresponding to a predetermined type or kind of cells. An electrical signal representing information on a pulse waveform corresponding to a distance to the detected type or kind of cells is generated. The electrical signal is applied to charging electrodes at an instant when the corresponding portion of the particle stream is formed into a droplet. The droplet is thus deflected by deflectors and is collected in a receptable. The electrical signal is thus supplied to the charging electrodes or a deflecting electric field when the corresponding particle passes thereby, so as to charge or deflect the particle in accordance with the detected type or kind.

In contrast to the conventional flow system method, in the method of the present invention, a high-intensity light pulse is used as an irradiation light source, and a change in the intensity of a preselected type of emitted light or a combination of types thereof over a period of time is measured to allow the selecting and/or sorting of minute particles.

The method and apparatus of the present invention are based on the following facts.

Minute particles themselves including a light-emitting substance (e.g., particles of a biological light-emitting substance) or minute particles with a coloring dye bound thereon are excited upon irradiation with high-intensity light, i.e., a light pulse tuned to the absorption band of molecules contained in the minute particles. The minute particles then emit light such as fluorescence or phosphorescence.

Light emitted from the molecules upon light pulse excitation undergoes a change in intensity over a period of time specific to the type of molecule involved. In other words, each type of molecule has a time interval specific thereto from a time at which the emitted light reaches a peak (rise time) to a time at which the emitted light after reaching its peak is attenuated and disappears (attenuation time). Thus, minute particles containing a particular type of molecules have a time interval specific thereto.

In each type of particle, the large proportion of normal cells of a particular type has a specific time interval, and the remaining proportion of abnormal cells of this particular type also has a specific time interval. Accordingly, if the specific time intervals for cells of a particular type are known, normal cells and abnormal cells of this type can be discriminated from each other.

The absorption band of molecules contained in minute particles includes an absorption band of the molecular skeleton of DNA bases, and another absorption band of a dye used, such as Acridine dye. Different information is obtained depending on which absorption band the irradiation light is tuned to.

FIGS. 1A and 1B show the state of light irradiation to explain the states of light emission and deactivation. The energy level is plotted along the axis of the ordinate. A straight arrow EX indicates laser beam absorption; a wavy arrow FL, fluorescence; and a broken arrow TR, energy transfer.

FIG. 1A corresponds to a case wherein a light pulse tuned to the absorption band of a dye is irradiated. The attenuation time of light emitted from the dye is used as a discrimination parameter. FIG. 1B corresponds to a case wherein a light pulse tuned to the absorption band of the molecular skeleton is irradiated. In this case, the attenuation time of light emitted from the molecular skeleton and the rise time of the light emitted from the dye are used as discrimination parameters.

The attenuation time of the emitted light can be used as a parameter since the deactivation process of the excited dye or the deactivation process of the molecules due to energy transfer into themselves or into the dye differs in accordance with the intermolecular reaction. The rise time of the emitted light can be used as a parameter since the bound state between the molecular skeleton and the dye, for example, the bond distance, is different for each type of combination, and hence the energy transfer from the molecular skeleton which has received light to the dye which emits light is different for each type of combination.

In the former case, when a fluorescent dye such as Acridine Orange R is inserted between cell DNA bases, abnormal cells such as cancerous cells take in the fluorescent dye in a large amount than do normal cells. When the abnormal cells are irradiated with a light pulse from an argon ion laser, the attenuation time of fluorescence thereof is longer than that of the normal cells.

In the latter case, in minute particles containing molecular skeletons which have different structures (e.g., abnormal cells among cells for one type can bond only weakly to a dye as compared to their normal counterparts), when a light pulse of a wavelength within the absorption band of the cells is irradiated, the abnormal and normal cells experience different rise times.

When the light pulse used for irradiation is linearly polarized light, molecules which have a transition moment in the direction of the electric vector of the irradiated light are selectively excited. The excited molecules are rotated due to thermodynamics and, following the loose anisotropy established immediately after excitation, become isotropic. The manner of such orientation relaxation can be acknowledged by the observation of a change in the polarization of fluorescence or the like over a period of time from the excited molecules.

The time required for the orientation relaxation (orientation relaxation time) is also specific to each of the molecules, i.e., differs depending upon the molecular size, the type of medium surrounding the molecules, and the degree of interaction of the molecules. If the orientation relaxation time required for each type of light pulse, e.g., fluorescence, can be determined, minute particles can be discriminated. In this case, regardless of whether a light pulse tuned to the molecular skeleton or to the dye is irradiated, the orientation relaxation time can be utilized as a discrimination parameter. For example, since the cell membrane is sensitive to anisotropy, this parameter can be effectively used for the discrimination of cells associated with cell membranes.

When the intensities of light emitted in the parallel direction (0°) and perpendicular direction (90°) with respect to a polarization angle of an excited light pulse are given as $I(0)$ and $I(90)$, respectively, emitted light polarization P is given as $P=(I(0)-I(90))/(I(0)+I(90))$ and anisotropy A is given as $A=(I(0)-I(90))/(I(0)+2I(90))$. Changes in these quantities over a period of time can be used as parameters for discriminating minute particles.

DESCRIPTION OF THE PREFERRED EMBODIMENT

The method and apparatus of the present invention will now be described in detail with reference to a case of the discrimination (sorting or selecting) of normal from abnormal cells.

Figure 2:
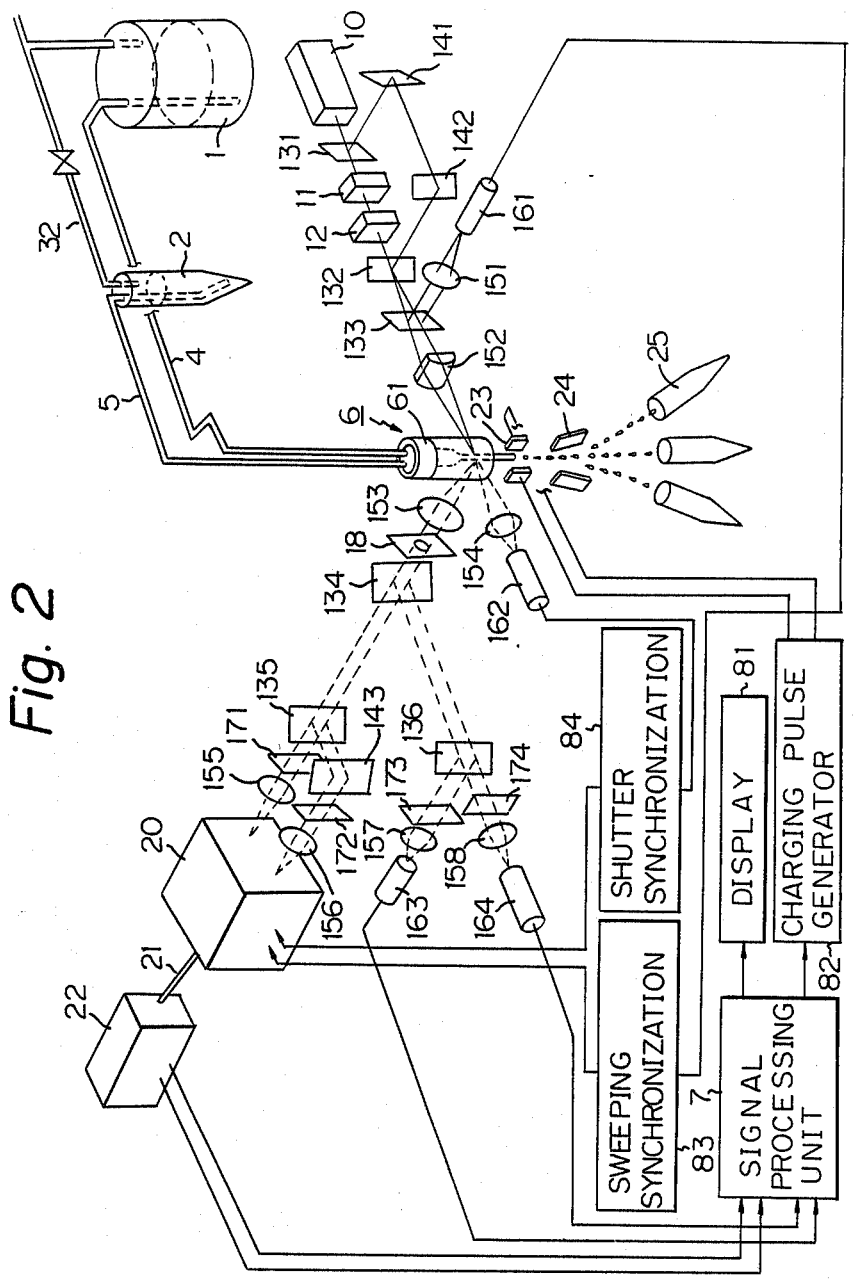
FIG. 2 is a perspective view of the overall configuration of an apparatus for discriminating (sorting or selecting) minute particles according to an embodiment of the present invention.
Figure 3:
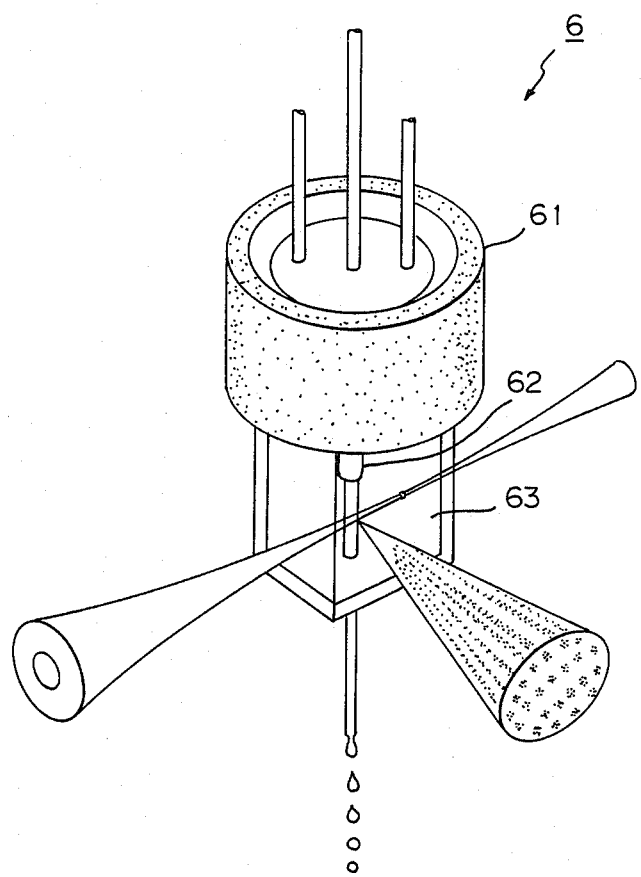
FIGS. 3 and 4 are perspective views showing examples of structurs of a flow chamber.
Figure 4:
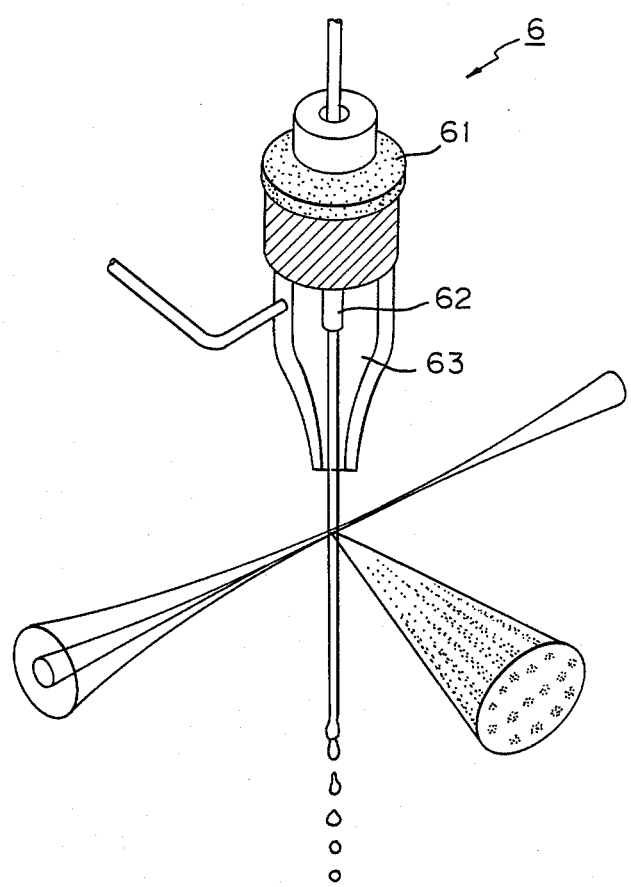

FIG. 2 is a perspective view of the overall configuration of an apparatus for discriminating (sorting or selecting) minute particles in accordance with an embodiment of the present invention. FIGS. 3 and 4 are perspective views showing examples of structures of a flow chamber in the apparatus shown in FIG. 2.

Cell samples are dyed with a suitable fluorescent dye as needed. A suitable dye is a dye having an absorption band of a light pulse upon being bound to cells, and is preferably a dye which is selectively bound to abnormal cells only. Examples of such dyes may include Feulgen dye or Acridine dye. Selective binding of a dye can be conveniently performed by binding a monoclonal antibody which is bound only to a specific portion of cells, and allowing the antigen to adsorb the desired dye.

Cell samples without a dye or cell samples with a suitable fluorescent dye bound thereto are suspended in a liquid such as physiological saline solution to provide an aqueous suspension. The suspension is filtered to remove any clumps of cells or foreign material, and the filtered suspension is held in a sample container 2. The suspension in the sample container 2 is compressed and is introduced into a flow chamber 6 through a tube 5. Compression is performed, for example, by a gas such as air, via a tube 32 shown in FIG. 2. Compression may be alternatively performed with a nonperistaltic pump or a peristaltic pump with peristaltic movement cancelling means. The suspension introduced into the flow chamber 6 is formed into a thin stream therein. The thin stream is concentrically surrounded by a cell-free liquid as a sheath liquid 63 such as a physiological saline solution. The sheath liquid 63 serves to locate the cells at the central axis of the apparatus and to define a distance to allow the selection or sorting of the cells. The stream is jetted through an exit nozzle 62 of the flow chamber 6.

The sheath liquid 63 in a container 1 is compressed and is supplied through a tube 4 to a sheath tube coaxially surrounding the exit nozzle 62 in the flow chamber 6. Pressure control of the sheath liquid and suspension is performed in such a manner that the individual cells are passed through the outlet nozzle one by one.

The flow chamber 6 may be of the submerged measurement type, as shown in FIG. 3. This flow chamber has a light source projection port and an observation port so that the thin stream is irradiated with a light pulse. An air measurement type flow chamber, as shown in FIG. 4, prepares a jet stream in such a manner that the jet flow from an exit nozzle is irradiated with a light pulse. Either of these two types of flow chamber can be used in the present invention. In either case, a droplet is formed which drips downward.

A vibration means 61 such as a piezoelectric crystal is mechanically connected to the upper part of the flow chamber. A liquid jet flow flowing from the flow chamber is regularly vibrated to form uniform droplets. Not all droplets necessarily contain cells and some may contain more than one cell. Although ideally each droplet contains one single cell, in practice one cell is found in several droplets.

Control of cell concentration is performed in accordance with the compression control of the cell suspension and sheath liquid, and with the frequency and value of a voltage applied to the piezoelectric crystal (generally a voltage of 15 V at a frequency of 40 to 50 kHz).

The cell stream in the form of the thin stream or jet stream is irradiated with a light pulse. A light source comprises, for example, an argon laser 10 having a mechanism for generating a light pulse by mode locking, a dye laser 11 for performing wavelength conversion and pulsewidth minimization, and a cavity dumper 12 for controlling the number of pulses.

The light pulse is used as a light source. A corresponding light beam to be used is a beam having an oscillation wavelength of the argon laser, typically strong at 488 nm or 514.5 nm and other ultraviolet regions, and a wavelength of the dye laser, such as about 600 nm if Rhodamine 6G is used as a dye. When beams of the two wavelengths are used, a double beam light source is obtained to allow selection of the optimal excitation wavelength of the cells.

To improve the S/N ratio of the laser beam of such a light pulse, such as a laser beam having a pulsewidth of 50 $\mu$sec to 50 nsec, the laser beam is focused in such a manner that its waist portion coincides with the thin stream, and is irradiated perpendicularly onto the thin stream.

A photodiode 162 located at the opposite side of the cell stream is directed toward the irradiation light source to detect whether a cell is within its detection range. The photodiode 162 supplies a signal for opening (releasing) a shutter of a streak camera 20. The light is pulsated. However, when a cell enters its detection range, the light is absorbed by the cell and the photodiode 162 produces a corresponding signal. This signal is used as a shutter open (release) signal.

When the cell does not interfere with the light pulse, fluorescence is not emitted and the streak camera 20 does not produce any signal other than a base noise. To eliminate this base noise, the output signal from the photodiode 162 is supplied to the streak camera 20. Then, when the cell does not interfere with the light pulse, a shutter sync signal is generated to set an acceleration voltage of an acceleration electrode 202 of the streak camera 20 at zero and the control voltage of a channel plate 204 thereof at zero. After the shutter is released and the acceleration electrode 202 and the channel plate 204 start operating, a shutter close signal is generated upon counting 100 pulses, or within 1 $\mu$s.

When a cell arrives at an intersection of the light pulse and the cell stream, the biological polymer in the cell or the dye bound thereto is excited to give off fluorescence. The fluorescence is focused in a direction perpendicular to both the cell flow and the irradiation direction of the light pulse by a focusing lens 153, and is supplied to the streak camera 20 and/or photoelectron multipliers 163 and 164. If required, deflectors 171 to 174 are arranged in front of these detecting means.

When the flow chamber used in the apparatus shown in FIG. 2 is not of the type shown in FIG. 3 or 4 but is of the type in which the cell stream flows parallel to or obliquely to the optical axis of the light pulse, the detection of emitted fluorescence need not be performed in the direction perpendicular to both the cell flow and the direction of irradiation of the light pulse. Here, it suffices to perform such detection only in such a manner that it is not interfered with by the influence of the incident light pulse.

A photoelectron multiplier or photodiode has a slow response time, and it cannot detect a light pulse having a duration shorter than the response time. Conversely, the time constant of the streak camera cannot be extended over a predetermined value. This is why both means are adopted in combination as a detecting means. For example, if the pulsewidth of the input light pulse is 0.1 nsec and has a repeating interval of 10 nsec, the number of pulses a cell receives during the time taken for the cell to pass through the light beam is 100 to 1,000.

Figure 5:
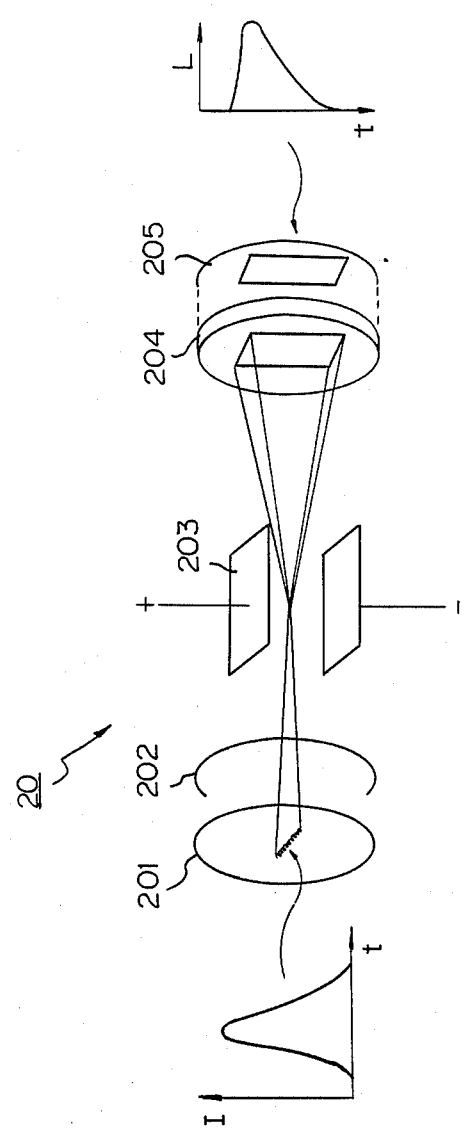
FIG. 5 is a representation explaing the mode of operation of a streak camera.

The mode of operation of the streak camera 20 will now be described with reference to FIG. 5. The emitted light pulse is incident on a photoelectric surface 201 to emit photoelectrons in accordance with a current intensity I. The photoelectrons are accelerated from the same initial velocity by the acceleration electrode 202 and are directed toward the channel plate 204, while they are vertically deflected in a deflection electric field vertical to the propagating direction of the electron beam and established by deflection electrodes 203.

A high-speed sweep voltage substantially synchronous with the emitted light pulse is applied to the deflection electrodes 203 in accordance with the synchro scan mode locking method. For this reason, the photoelectrons which are emitted with a time lag become incident on the lower portion of the channel plate 204, are multiplied, bombarded against the phosphor screen, and converted into light. As a result, an image having a brightness L corresponding to the intensity of the fluorescence pulse is displayed on the phosphor screen, whereon time is plotted along the axis of the ordinate. Although a photoelectron beam is generated for each phosphor screen and is swept at high speed, the image displayed on the screen is an image for each cell due to the after-image effect.

The image is supplied to a light-receiving element 22 such as an image pickup tube or diode array through an output relay lens, an optical fiber 21, and so on. An electrical signal obtained by scanning the light-receiving element represents a change in the intensity of the emitted light pulse over a period of time.

A high-speed sweep voltage to be applied to the deflection electrodes 203 is synchronized with the emitted light pulse by a sweep synchronizing circuit, which uses an output from the photodiode 162 corresponding to the irradiated light pulse for achieving synchronization.

Figure 1A:
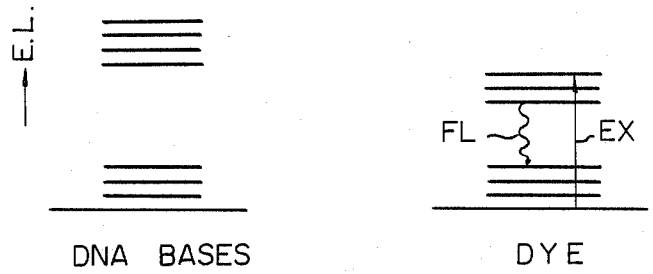
FIGS. 1A and 1B are representations explaining the states of light emission and the deactivation of particles upon light irradiation.

If satisfactory analysis cannot be performed unless light emission from the molecular skeleton such as the DNA molecular skeleton can be discriminated from that from the dye, as in the case of the light emission shown in FIG. 1(A), band-pass filters corresponding to the respective light emission wavelengths can be inserted before the streak camera.

The orientation relaxation time can be detected by the streak camera in the manner described below. According to one method, the emitted light pulse is split into two pulses, which are supplied to deflectors 171 and 172 having deflection angles 0° and 90°, respectively. The pulses are detected by the corresponding one of two streak cameras. According to another method, two fluorescent pulses having deflection angles 0° and 90°, respectively, are supplied to right and left halves of a single streak camera. Two corresponding images are displayed on the phosphor screen, and corresponding electrical signals are obtained.

If the irradiated light pulse is a laser pulse as described above, the emitted light pulse is also generally linearly polarized light. In this case, in order to measure the attenuation time of emitted light without an influence of the polarization, observation can be performed through a polarizer having as a polarization angle a so-called magic angle, namely 54.7°.

When the photoelectron multipliers or photodiodes 163 and 164 are used as the means for detecting the emitted light pulses, a single pulse among a number of pulses generated for each cell can be detected to determine the rise time of the emitted light, the attenuation time thereof, and the orientation relaxation time. An average value of several pulses for each cell can be calculated to attain a high sensitivity.

The electric signals from the streak camera and the photoelectron multipliers or photodiodes are counted by the time constant counting circuit, to be described later, so as to calculate the rise time of the emitted light, the attenuation time thereof, and the orientation relaxation time.

Figure 1B:
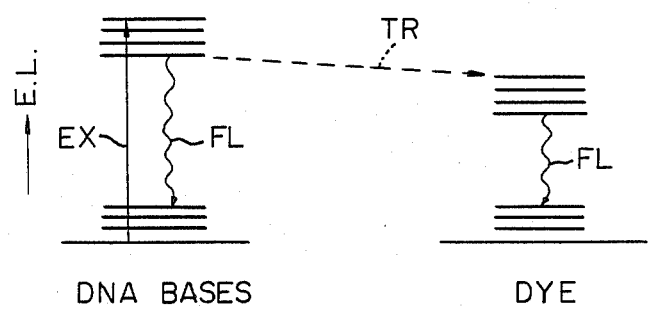
Figure 6:
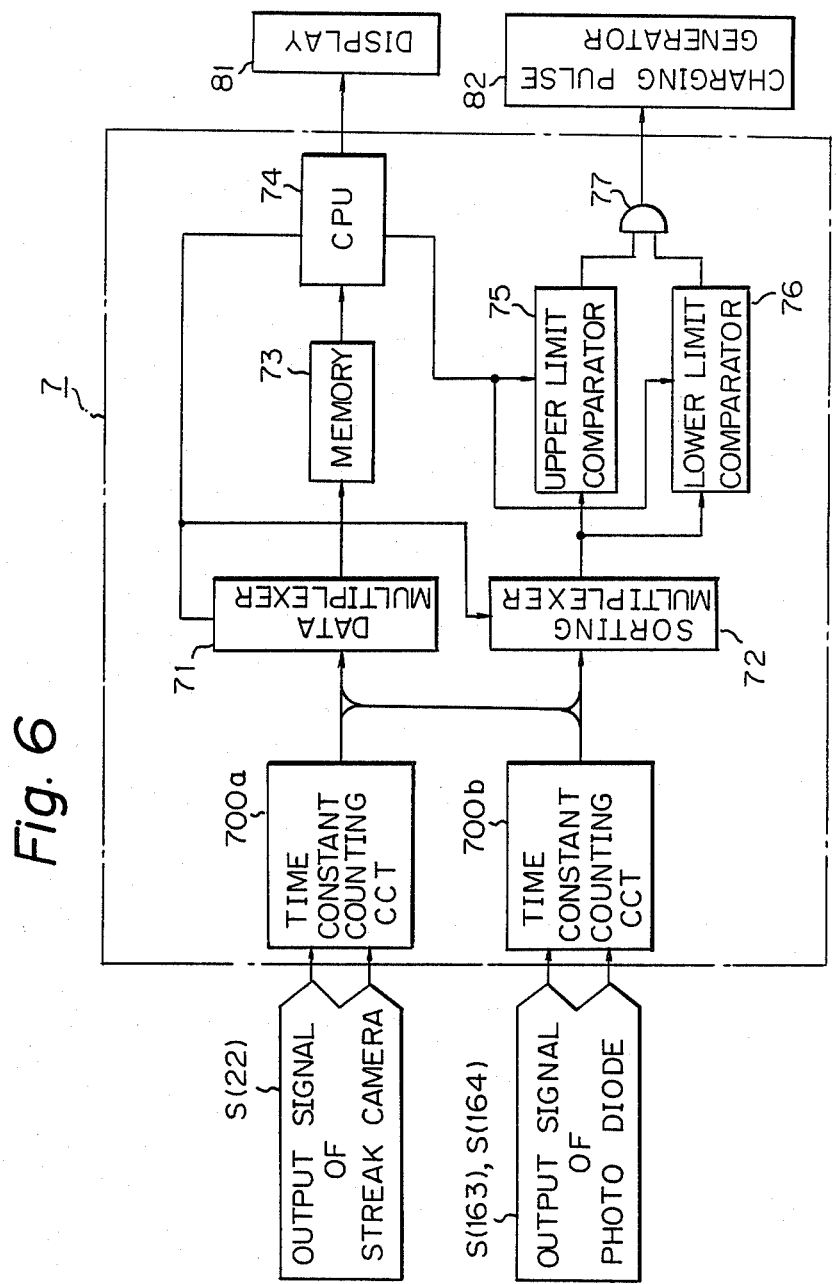
FIG. 6 is a block diagram of the configuration of a signal processing section of the apparatus shown in FIG. 1.

FIG. 6 shows the configuration of a signal processing unit 7 of the apparatus shown in FIG. 1.

The rising-up time of emitted light, the attenuation time thereof, and the orientation relaxation time as calculation outputs from time constant counting circuits 700a and 700b are supplied to a data multiplexer 71 and sorting multiplexer 72.

In accordance with an instruction from a central processing unit (CPU) 74, the data multiplexer 71 sequentially switches the signals of the respective sensors and writes the signals in a memory 73. In response to an instruction from the CPU 74, the signals written in the memory 73 are read out and displayed on a display 81 such as a CRT as data in the form of a graph or the like. The signals read out from the memory 73 can also be supplied to a printing device to produce a hard copy.

When the elements to be sorted, that is, elements of the rising-up time, the attenuation time, and the orientation relaxation time, are set, in response to an instruction from the CPU 74, the sorting multiplexer 72 selects one or more elements, which are supplied to one or more upper or lower limit comparators 75 or 76, respectively. Each of the upper or lower comparators compares the input signal with a predetermined reference value. When the input signal falls within a predetermined range (between the upper and lower limits), a charging pulse generator 82 generates a deflection signal with a predetermined delay time, for example, about 500 to 1,000 μs.

In this manner, the rising-up time of fluorescence, the attenuation time thereof, and the orientation relaxation time of each cell are compared with the reference values corresponding to the values of a normal cell of the type under examination. The cell is discriminated in accordance with a deviation from the reference value, and a corresponding deflection signal is produced for sorting the cell.

Charging electrodes 23 are arranged to sandwich the portion at which a droplet is formed from the cell stream. In accordance with the deflection signal as described above, pulse voltages of ±50 to 300 V having a pulsewidth of 50 to 200 μs from the charging pulse generator 82 are applied to the charging electrodes 23. When a droplet is formed, it is immediately charged by the charging electrodes 23 which have received the corresponding charging pulses. As described above, as each cell passes between the charging electrodes 23, the cell is charged to a degree corresponding to its type (normal/abnormal), since the corresponding signal obtained by the series of operations comprising light irradiation, detection of emitted fluorescence, comparison, and calculation has been delayed.

The droplet then passes through the gap between two deflectors 24 which sandwich therebetween the droplet path and which have a distance of 2 to 5 cm therebetween. A voltage of ±1,500 to 2,000 V is applied to the deflectors 24, and the charged droplet is deflected by static electricity and is collected in a receptacle 25 positioned 4 to 5 cm below the deflectors 24. The noncharged droplet is not deflected and drops straight.

The deflection signal need not always be supplied to the charging pulse generator. In this case, the charging electrodes can charge each cell to the same degree. However, the deflection signal is supplied to a circuit for driving the electric field of the deflectors so as to change the deflecting degree of each cell.

The time relationships among the particle stream, the irradiated light pulse, the emitted light pulse, the shutter gate of the streak camera, the sweep voltage of the streak camera, and the charging electric field applied to a droplet will now be described with reference to the timing charts shown in FIG. 7.

Figure 7:
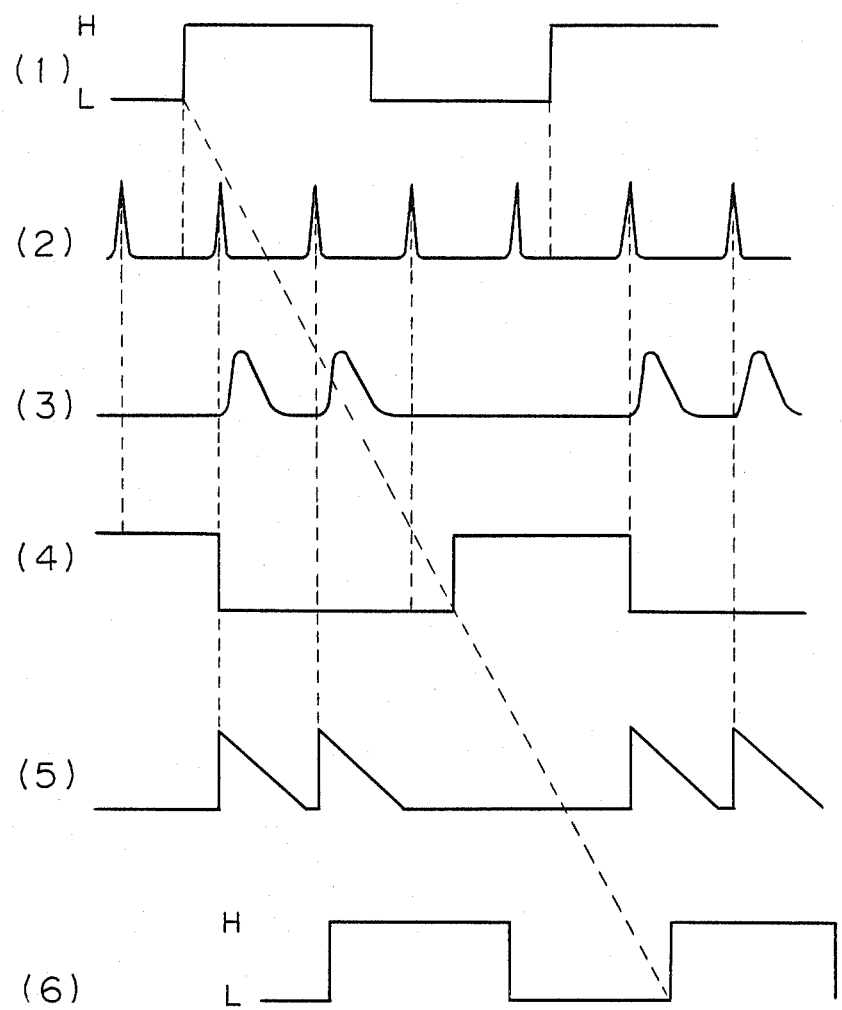
FIG. 7 shows timing charts of the signals at respective parts of the apparatus shown in FIG. 1.

In FIG. 7(1), which represents the particle stream, a state wherein a minute particle crosses the light pulse is assigned H level and a state wherein a minute particle does not cross the light pulse is assigned L level. FIG. 7(2) represents an irradiated light pulse, while FIG. 7(3)

represents an emitted light pulse. FIGS. 7(4) and 7(5) respectively represent a voltage of the shutter gate of the streak camera and the sweep voltage of the streak camera. FIG. 7(6) represents two levels of a voltage applied to the charging electrodes. When a pulse appears in FIG. 7(2), a pulse in FIG. 7(3) appears after a slight time delay corresponding to the rising-up time of emitted light, reaches a peak and then attenuates gradually.

Although there is actually a time lag in the period of the voltage shown in FIG. 7(5) which corresponds to the time required for the light to travel from the light source to the streak camera, it is neglected in FIG. 7(5) for simplicity. The high level of the voltage shown in FIG. 7(6) is delayed for a time interval from the irradiation of the minute particle with the light pulse to the charging of the droplet with the charging electrodes. Although this time lag is almost comparable with the time lag of the signal of FIG. 7(5) from that of FIG. 7(2), it is exaggerated in FIG. 7(6) for easy understanding.

Figure 8:
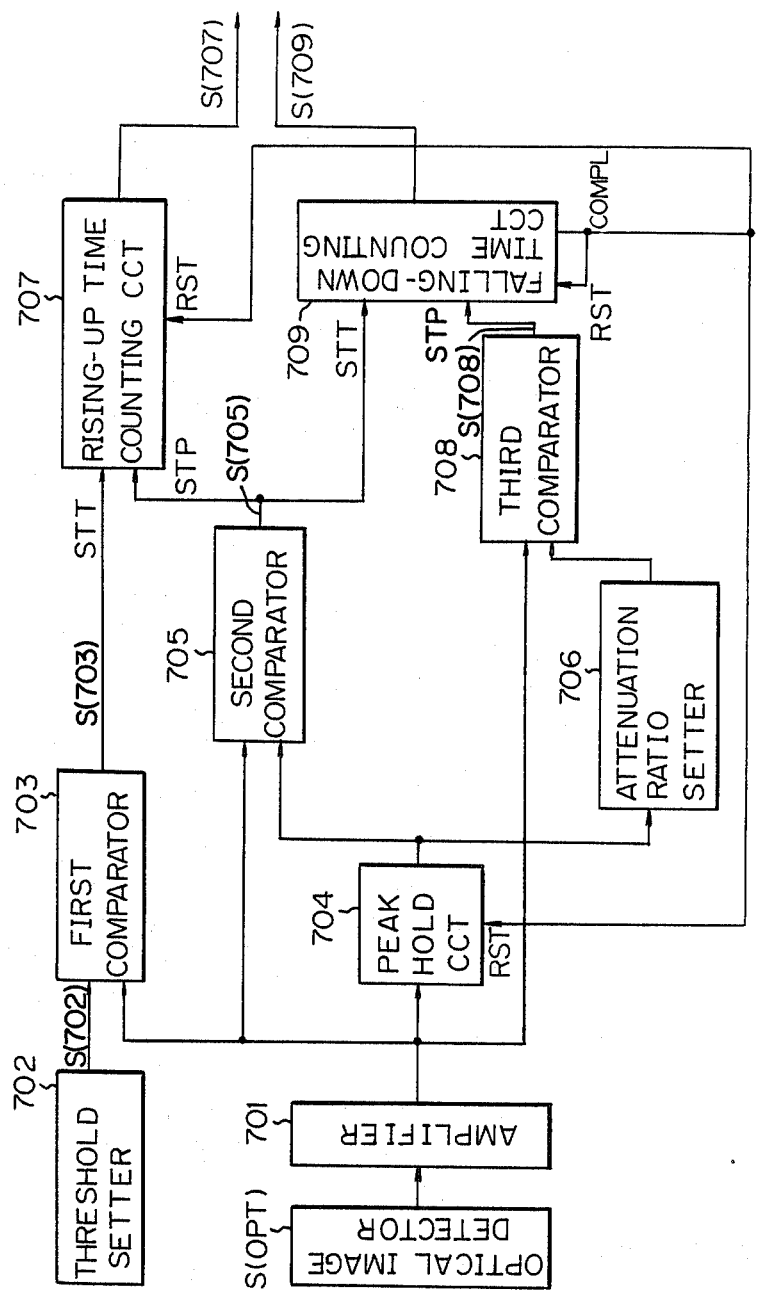
FIGS. 8 and 9 are block diagrams of a time constant counter circuit in the circuit shown in FIG. 6.
Figure 9:
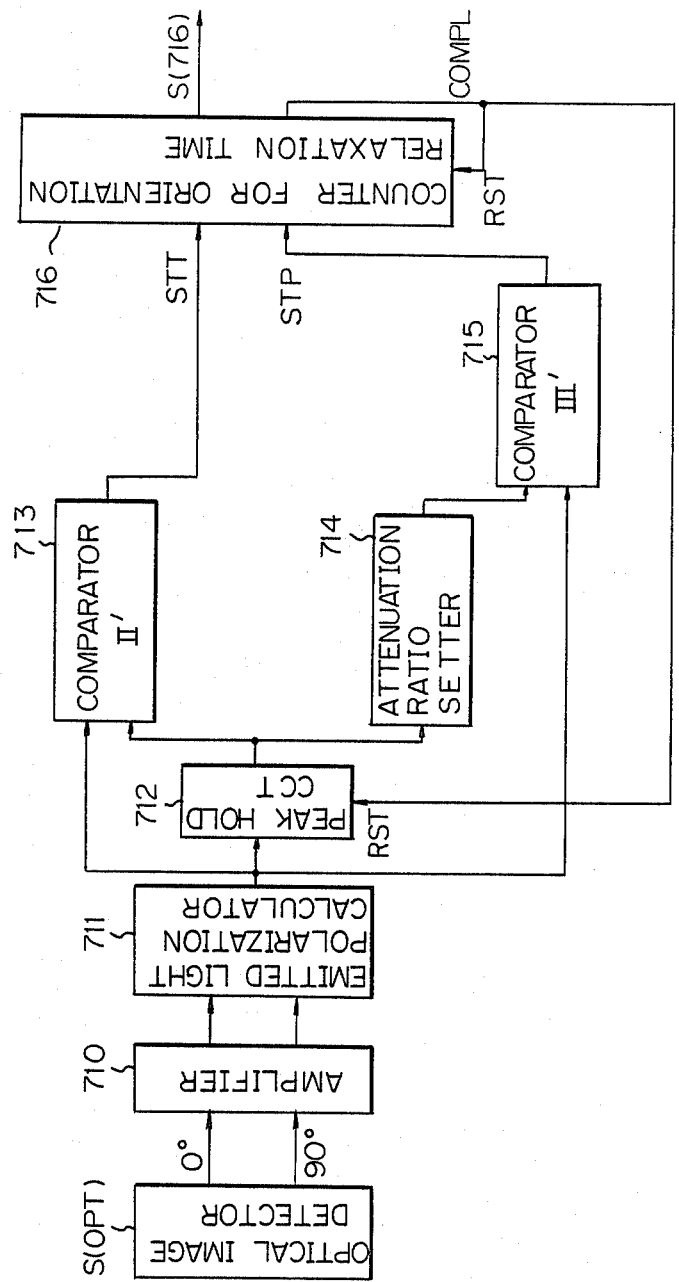

FIGS. 8 and 9 show the configuration of the time constant counting circuits in the circuit shown in FIG. 6. When the time constant counting circuits 700a and 700b are used to count the rising-up time or attenuation time of the emitted light pulse, they have the configuration as shown in FIG. 8.

In the circuit shown in FIG. 8, in order to measure the rising-up time of the emitted light, an electrical signal S(OPT) obtained by conversion of an image (either without polarization or polarized through a predetermined polarization angle, e.g., 54.7°) is preamplified by an amplifier 701 and is subjected to preprocessing such as smoothing. A rising-up time reference signal S(703) is set by a first comparator 703. The signal S(703) is set in accordance with a signal S(702) of a threshold setter 702. The threshold is determined in accordance with the time at which the light emission signal rises up (emitted light pulse), the noise of the optical system or the electrical system up to this time constant counting circuit, and the like.

The rising-up time peak signal is obtained as a signal S(705) from a second comparator 705. The second comparator 705 compares the light emission signal from the amplifier 701 with a signal from a peak hold circuit 704 and produces a peak signal when the light emission signal becomes greater than the other signal. A rising-up time counting circuit 707 counts a time difference between the rising-up edges of the signals S(703) and S(705) so as to measure the rising-up time of emitted light.

In order to measure the attenuation time of emitted light, the second comparator 705 detects the time at which the ligh emission signal reaches a peak. More specifically, the light emission signal from the amplifier 701 is compared with the signal from the peak hold circuit 704 by the second comparator 705. When the light emission signal becomes smaller than the other signal, the output from the second comparator 705 is inverted. The thus-inverted output from the second comparator 705 is used as a reference signal to start counting the attenuation time.

The attenuation time may be defined as a time during which the signal peak is attenuated to 1/e (63%). This value 1/e or another suitable value is set in an attenuation ratio setter 706. The value from the setter 706 and the light emission signal from the amplifier 701 are supplied to a third comparator 708. When the magnitude relationship of the two signals is inverted, an output signal S(708) is produced from the third comparator 708. Measurement of the falling-down time is performed by falling-down time counting circuit 709. A signal STT is used to start counting the falling-down time, and a signal STP is used to stop counting it.

A count end signal COMPL from the falling-down time counting circuit 709 resets itself, the rising-up time counting circuit 707, and the peak hold circuit 704. In this manner, the circuit shown in FIG. 8 produces a rising-up time count signal S(707) and a falling-down time count signal S(709).

When the time constant counting circuit is used to calculate the orientation relaxation time, it has the configuration as shown in FIG. 9. Referring to FIG. 9, electrical signals S(OPT) corresponding to polarization angles 0° and 90° and produced from the image detecting means are preamplified by an amplifier 710 and are supplied to an emitted light polarization calculator 711 to calculate the value corresponding to the degree of polarization. An output from the circuit 711 is processed in a similar manner as for the calculation of the attenuation time. In this manner, the circuit in FIG. 9 produces an orientation relaxation time count signal S(716).

One or both of the circuits shown in FIGS. 8 and 9 can be used for the time constant counting circuits of the circuit shown in FIG. 6, as required. When the circuit shown in FIG. 8 is used for the time constant counting circuit, one of the signals S(707) and S(709) can be omitted.

In the apparatus shown in FIG. 2, the parameter for selecting and sorting the minute particles is based on a difference in the local structure at the molecular level of the minute particles. In particular, it is directed to the molecular biological or molecular chemical cell level, or the chromosome level or biomolecular level when biological minute particles are concerned. More specifically, the parameter is associated with, first, the distance betwene the respective parts of each constituent molecule, e.g., the distance of the nucleic acid-base pair or the distance between the dye molecule and the molecular skeleton. Second, it is associated with the size or type of particles such as nucleic acid or proteins. Third, it is associated with the molecular structure such as the pitch of the double helix, the internal oscillation of the molecule, the Brownian movement, the chain bending, and information on the local rotary movement of the molecule. Fourth, the parameter is associated with the detection of the transient intermediate products of a biological chemical reaction including a photochemical reaction. Fifth, it is associated with information on a region of a cell, such as the bonded state between the cell membrane and the proteins, or the membrane thickness. Sixth, it is associated with information on other properties of biological minute particles, such as the fused state of the cell, surface lectin receptors distribution, or proximity of chromatin.

The above information is highly significant information directly related to abnormal factors in the biological minute particles. The apparatus in FIG. 2 can select and sort a large population sample of biological minute particles within a short period of time in accordance with such highly significant information. The apparatus is useful in clinical applications and fundamental medical studies and can be used for selecting and sorting other types of minute particles.

The present invention is not limited to the embodiments described above, and various other changes and modifications can be made. The method and apparatus of the present invention may be used in combination with a volume detection system using a Coulter orifice, as described in Japanese Examined Patent Publication (Kokoku) No. 56-13266, or a parameter which is obtained by converting pulsed fluorescence or scattered light from particles irradiated with a light pulse and detecting the intensity of the obtained continuous light, i.e., by a conventional flow system analysis technique.

I claim:

1. A method of discriminating minute particles, comprising the steps of:
    producing a stream of minute particles, in which substantially each of said minute particles is separated from the adjacent particle with an interval, from a suspension of said minute particles;
    irradiating said produced stream of minute particles with high-intensity light pulses directed from a light source through a cavity dumper for controlling the number of light pulses;
    detecting the intensity of light emission from said irradiated particles by a streak camera;
    discriminating the particles in said stream by the intensity of light emission from said irradiated particles; and
    changing said irradiated stream of minute particles into a sequence of droplets;
    wherein said discrimination is carried out on the basis of characteristics of the change, with time, of the intensity of said light emission, represented by at least one of a rise time of the emitted light, an attenuation time of the emitted light and an orientation relaxation time, using the result of the detection of the intensity of light emission from said irradiated particles by the streak camera.

2. The method according to claim 1, wherein said streak camera is of the synchro scan type.

3. The method according to claim 2, further comprising a step of data analysis for calculating, treating, and discriminating a streak image obtained by said streak camera.

4. An apparatus for discriminating minute particles, comprising:
    a flow chamber;
    a means for introducing a suspension of the minute particles into said flow chamber, producing a particle stream with the individual minute particles substantially separated from each other, and changing said particle stream into a sequence of droplets;
    a means for generating high-intensity light pulses;
    a means for irradiating said produced particle stream with the high-intensity light pulses including a cavity dumper located in the path of the light pulses for controlling the number of light pulses irradiated onto said particle stream;
    a streak camera for detecting light emission from said irradiated particles; and
    a means for calculating the characteristics of the change, with time, of the intensity of said light emission, represented by at least one of a rise time of the emitted light, an attenuation time of the emitted light and an orientation relaxation time, on the basis of the detection by said streak camera for detecting light emission.

5. The apparatus according to claim 4, wherein said streak camera is of the synchro scan type.

6. The apparatus according to claim 5, further comprising a data analyzing means for calculating, treating, and discriminating a streak image obtained by said streak camera.

* * * * *